United States Patent
Hsieh et al.

(10) Patent No.: US 10,282,964 B2
(45) Date of Patent: May 7, 2019

(54) GAS DETECTING DEVICE

(71) Applicant: Winbond Electronics Corp., Taichung (TW)

(72) Inventors: Ming-Hung Hsieh, Taichung (TW);
Yu-Hsuan Ho, Taichung (TW);
Ming-Chih Tsai, Taichung (TW);
Yen-Jui Chu, Taichung (TW)

(73) Assignee: Winbond Electronics Corp., Taichung (TW)

( * ) Notice: Subject to any disclaimer, the term of this patent is extended or adjusted under 35 U.S.C. 154(b) by 30 days.

(21) Appl. No.: 15/594,669

(22) Filed: May 15, 2017

(65) Prior Publication Data

US 2018/0202956 A1 Jul. 19, 2018

(30) Foreign Application Priority Data

Jan. 16, 2017 (CN) .......................... 2017 1 0032425

(51) Int. Cl.
| | | |
|---|---|---|
| *G01N 27/04* | (2006.01) | |
| *G01N 33/00* | (2006.01) | |
| *G08B 21/12* | (2006.01) | |
| *G01N 27/12* | (2006.01) | |
| *G08B 21/14* | (2006.01) | |

(52) U.S. Cl.
CPC .......... *G08B 21/12* (2013.01); *G01N 27/125* (2013.01); *G01N 33/0036* (2013.01); *G08B 21/14* (2013.01)

(58) Field of Classification Search
CPC .... G01N 27/02; G01N 27/04; G01N 33/0006; G01N 33/0009; G01N 33/0036; G08B 21/12
See application file for complete search history.

(56) References Cited

U.S. PATENT DOCUMENTS 4,872,759 A * 10/1989 Stich-Baumeister ......................
G01N 21/7703
356/432
6,606,897 B1 8/2003 Koyano et al.
(Continued)

FOREIGN PATENT DOCUMENTS

| CN | 2713470 | 7/2005 |
|---|---|---|
| TW | M471557 | 2/2014 |

*Primary Examiner* — Huy Q Phan
*Assistant Examiner* — David B Frederiksen
(74) *Attorney, Agent, or Firm* — JCIPRNET

(57) ABSTRACT

A gas detecting device configured to be attached to a surface includes a substrate, a semiconductor layer, a light-emitting component, a first electrode and a second electrode. The substrate includes a plurality of stacking layers stacked onto one another, and a material of the substrate includes cellulose nanofibrils (CNF). The substrate is formed by 3-D printing, such that a contact surface of the substrate is tightly attached to the surface. The semiconductor layer is formed on the substrate by 3-D printing. The light-emitting component is disposed on the substrate. The first electrode is coupled to the semiconductor layer and the light-emitting component. The second electrode is coupled to the semiconductor layer and a ground electrode. The first electrode and the second electrode are both disposed on the semiconductor layer and maintain a gap therebetween. A resistance of the semiconductor layer is changed according to a concentration of a designated gas.

10 Claims, 2 Drawing Sheets

(56) References Cited

U.S. PATENT DOCUMENTS

| | | | | |
|---|---|---|---|---|
| 6,623,618 | B1* | 9/2003 | Kato | G01N 27/419 |
| | | | | 204/425 |
| 9,437,628 | B1* | 9/2016 | Ma | H01L 27/13 |
| 2002/0030196 | A1* | 3/2002 | Iwata | H01L 33/285 |
| | | | | 257/102 |
| 2007/0056352 | A1* | 3/2007 | Birkhofer | G01N 33/0054 |
| | | | | 73/23.21 |
| 2009/0084160 | A1* | 4/2009 | Bristol | G01D 11/245 |
| | | | | 73/31.05 |
| 2012/0161253 | A1* | 6/2012 | Hsieh | G01N 27/128 |
| | | | | 257/414 |
| 2014/0296687 | A1* | 10/2014 | Irazoqui | A61B 3/16 |
| | | | | 600/398 |
| 2016/0007894 | A1* | 1/2016 | Kahlman | A61B 5/6833 |
| | | | | 600/323 |
| 2017/0003238 | A1* | 1/2017 | Salvador | G01N 27/04 |
| 2017/0254779 | A1* | 9/2017 | Wang | G01N 27/125 |
| 2017/0355143 | A1* | 12/2017 | Speckmann | B33Y 10/00 |
| 2018/0045698 | A1* | 2/2018 | Sultana | G01N 33/0027 |

* cited by examiner

GAS DETECTING DEVICE

CROSS-REFERENCE TO RELATED APPLICATION

This application claims the priority benefit of China application serial no. 201710032425.4, filed on Jan. 16, 2017. The entirety of the above-mentioned patent application is hereby incorporated by reference herein and made a part of this specification.

BACKGROUND

Technical Field

The disclosure relates to a detecting device, and particularly to a gas detecting device.

Description of Related Art

Along with development of technology, semiconductor applications have become more and more prevalent in daily life. Rise of the chemical engineering industry and massive use of internal combustion engines (i.e., motors) have caused increasingly serious environmental pollution in which air pollution has the most direct impact on daily life. Nowadays, since air pollution sources gradually increase, it has become a trend to detect abnormal environmental conditions anytime and anywhere by a gas sensor. In numerous applications, gas detecting devices made using semiconductors by exploiting the fact that semiconductors are highly sensitive to gases in contact therewith have received more and more attention. In detail, when a semiconductor for gas detection contacts a designated gas, electrical properties of the semiconductor are changed accordingly. Therefore, by detecting the electrical properties of the semiconductor, a user may observe whether the designated gas is present in the environment where the semiconductor is located.

However, unlike wallets, mobile phones and so on, gas detecting devices currently are not what people always carry with themselves. Moreover, they have larger volume and greater overall thickness, making them not easy to carry along, and burdens of carrying are even increased. In addition, people are apt to forget to bring them. Therefore, how to improve portability of the gas detecting devices and to simplify interpretation of detection results has become an important issue in this field.

SUMMARY

The disclosure provides a gas detecting device which is tightly attached to a user's cloth or skin for ease of carry and which facilitates interpretation of a result of gas detection.

The gas detecting device of the disclosure is configured to be attached to a surface, and includes a substrate, a semiconductor layer, a light-emitting component, a first electrode and a second electrode. The substrate comprises a plurality of stacking layers stacked onto one another, and a material of the substrate includes cellulose nanofibrils, wherein the substrate is formed by a 3-D printing technique, such that a contact surface of the substrate is tightly attached to the surface. The semiconductor layer is formed on the substrate by the 3-D printing technique. The light-emitting component is disposed on the substrate. The first electrode is coupled to the semiconductor layer and the light-emitting component. The second electrode is coupled to the semiconductor layer and a ground electrode. The second electrode and the first electrode are both disposed on the semiconductor layer and maintain a gap therebetween. A resistance of the semiconductor layer is changed according to a concentration of a designated gas.

In an embodiment of the disclosure, a greatest thickness of the substrate ranges from 10 μm to 100 μm.

In an embodiment of the disclosure, the contact surface is a flat surface so as to conform to a flat-surface profile of the surface.

In an embodiment of the disclosure, the contact surface is a curved surface so as to conform to a curved-surface profile of the surface.

In an embodiment of the disclosure, the gas detecting device further includes an adhesive layer disposed on the contact surface so as to attach the substrate to the surface.

In an embodiment of the disclosure, the semiconductor layer is a metal oxide layer.

In an embodiment of the disclosure, a material of the semiconductor layer includes an oxide of graphene, tin, zinc, indium, tungsten, magnesium, iron or titanium.

In an embodiment of the disclosure, the resistance of the semiconductor layer is inversely proportional to the concentration of the designated gas.

In an embodiment of the disclosure, the light-emitting component includes a light-emitting diode.

In an embodiment of the disclosure, the first electrode, the second electrode and the light-emitting component are formed by the 3-D printing technique.

Based on the above, in the disclosure, the substrate and the semiconductor layer in the gas detecting device are formed by the 3-D printing technique. Thus, bonding strength between the substrate and the semiconductor layer of the gas detecting device is improved. Moreover, the contact surface of the substrate that contacts a user's body surface is designed according to a profile of the user's body surface, so as to print the substrate accordingly. Therefore, the contact surface of the substrate in the disclosure is tightly attached to the user's surface. In addition, the substrate formed by 3-D printing is capable of effectively reducing the thickness thereof. Therefore, the substrate formed by 3-D printing effectively enhances fitness and user comfort of the gas detecting device.

In addition, the material of the substrate includes cellulose nanofibrils which have high structural strength and light weight and are both ductile and strong. Therefore, the substrate printed with cellulose nanofibrils has not only high structural strength but also less weight, and may thus be attached to the user's surface without falling off easily or causing the user discomfort. Moreover, the disclosure utilizes the characteristic that the resistance of the semiconductor layer is changed according to the concentration of the designated gas. When the concentration of the designated gas is higher than a predetermined value, the semiconductor layer conducts the first electrode and the second electrode, so as to conduct the light-emitting for light emitting, and thereby enable the user to interpret a detecting result of gas detection easily.

To make the above features and advantages of the disclosure more comprehensible, embodiments accompanied with drawings are described in detail as follows.

DETAILED DESCRIPTION OF DISCLOSED EMBODIMENTS

Figure 1:
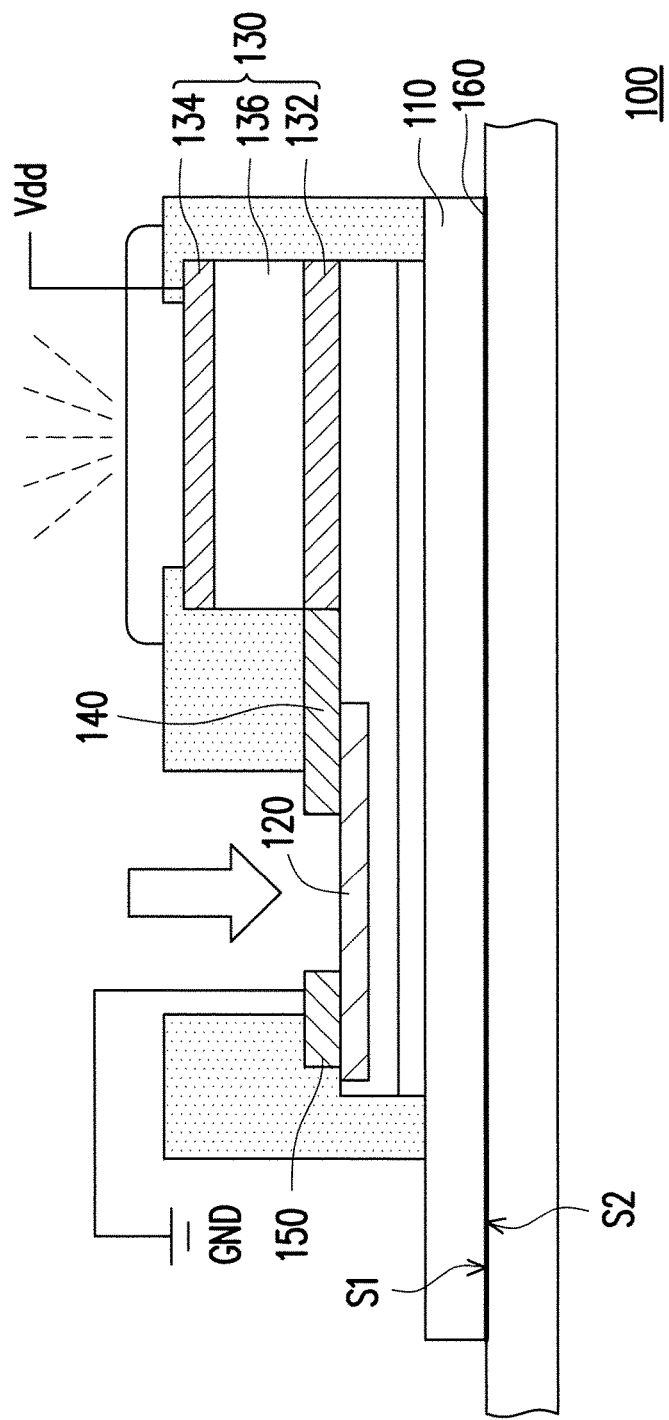
FIG. 1 is a schematic cross-sectional view of a gas detecting device according to an embodiment of the disclosure.
Figure 2:
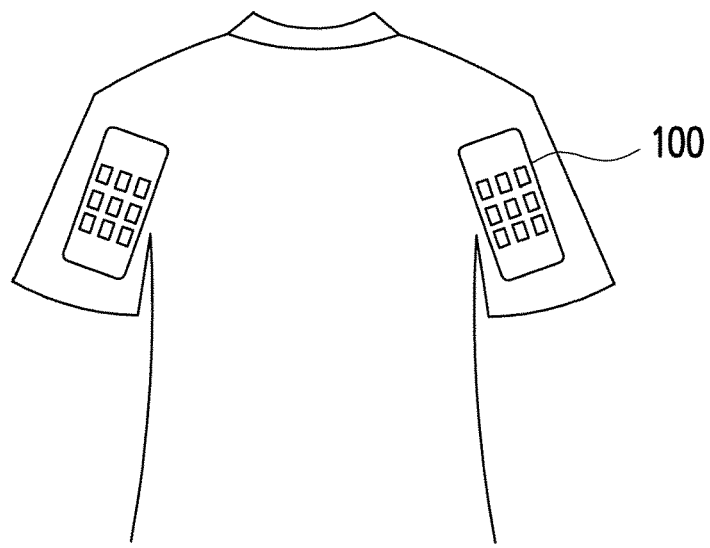
FIG. 2 is a schematic view of a use scenario of a gas detecting device according to an embodiment of the disclosure.
Figure 3:
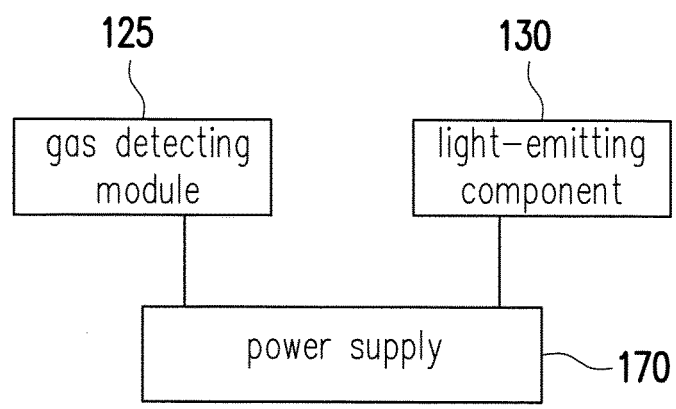
FIG. 3 is a schematic block diagram of a gas detecting device according to an embodiment of the disclosure.

FIG. 1 is a schematic cross-sectional view of a gas detecting device according to an embodiment of the disclosure. FIG. 2 is a schematic view of a use scenario of a gas detecting device according to an embodiment of the disclosure. FIG. 3 is a schematic block diagram of a gas detecting device according to an embodiment of the disclosure. Referring to FIG. 1 to FIG. 3 together, in the present embodiment, a gas detecting device 100 is attached to a user's surface as shown in FIG. 2. The "surface" as used herein refers to a body surface of the user's cloth or skin, which may be a flat surface, or a regular/irregular curved surface. The present embodiment is not limited thereto. As shown in FIG. 1, the gas detecting device 100 of the present embodiment includes a substrate 110, a semiconductor layer 120, a light-emitting component 130, a first electrode 140 and a second electrode 150. In the present embodiment, the substrate 110 is formed by a three-dimensional (3-D) printing technique. In the present embodiment, the substrate 110 of the gas detecting device 100 is printed out using a 3-D printing device according to a digital 3-D model of the substrate 110.

For example, the digital 3-D model may be a digital 3-D image file built by computer-aided design (CAD) or animation and modeling software or the like. The digital 3-D model is sliced into a plurality of cross sections for the 3-D printing device to read and form building materials layer by layer on a printing platform of the 3-D printing device according to the cross sections of the digital 3-D model, and thereby forms a plurality of stacking layers. The stacking layers are stacked onto one another to form the substrate 110. That is, the substrate 110 formed by 3-D printing includes a plurality of stacking layers stacked on top of one another.

In the present embodiment, the whole gas detecting device 100 (including the substrate 110, the semiconductor layer 120, the light-emitting component 130, the first electrode 140 and the second electrode 150) may be formed by the 3-D printing technique, so as to improve bonding strength between the components of the gas detecting device 100. The 3-D printing techniques in the present embodiment may include stereo-lithography, fused filament fabrication (FFF), melted and extrusion modeling, electron beam modeling or other suitable 3-D printing techniques. The disclosure is not limited thereto.

In the present embodiment, since at least the substrate 110 in the gas detecting device 100 is formed by 3-D printing, a contact surface S1 of the substrate 110 that contacts the user's surface is designed according to a profile of the user's surface, so as to print the substrate 110 accordingly. In detail, if the user's surface S2 is a flat surface, according thereto, the contact surface S1 of the substrate 110 is designed and printed as a flat surface conforming to the flat-surface profile of the user's surface S2. Similarly, if the user's surface S2 is a curved surface, according thereto, the contact surface S1 of the substrate 110 is designed and printed as a curved surface conforming to the curved-surface profile of the user's surface S2. Therefore, the contact surface S1 of the substrate 110 of the present embodiment is tightly attached to the user's surface S2. In addition, the 3-D printing device is capable of printing out the substrate 110 having an extremely thin thickness. That is, the substrate 110 formed by 3-D printing is effectively reduced in thickness. In the present embodiment, the greatest thickness of a substrate ranges from 10 μm to 100 μm. Therefore, the substrate 110 formed by 3-D printing effectively enhances fitness and user comfort of the gas detecting device 100.

In addition, in the present embodiment, a material of the substrate 110 includes cellulose nanofibrils (CNF), a fibrous material produced by decomposing vegetable fibers and having a diameter of merely 3 nm to 4 nm. Cellulose nanofibrils have high structural strength and light weight, and are both ductile and strong. Generally, the weight of cellulose nanofibrils is merely one-fifth of the weight of iron, while the strength of cellulose nanofibrils is five times or more the strength of iron. Therefore, the substrate 110 printed with cellulose nanofibrils has not only high structural strength but also less weight, and may thus be easily attached to the user's surface S2 without falling off easily or causing the user discomfort. In the present embodiment, the gas detecting device 100 further includes an adhesive layer 160 disposed on the contact surface S1 of the substrate 110, so as to attach the substrate 110 to the body surface S2.

In the present embodiment, the semiconductor layer 120 is also formed on the substrate 110 by 3-D printing, so as to improve bonding strength between the semiconductor layer 120 and the substrate 110. The light-emitting component 130 is disposed on the substrate 110. Both of the first electrode 140 and the second electrode 150 are disposed on the semiconductor layer 120, wherein the first electrode 140 is coupled to the semiconductor layer 120 and the light-emitting component 130. The second electrode 150 is coupled to the semiconductor layer 120 and a ground electrode GND, and a gap is maintained between the first electrode 140 and the second electrode 150, as shown in FIG. 1. Under such arrangement, the first electrode 140 and the second electrode 150 are electrically conductive to each other via the semiconductor layer 120, and a resistance of the semiconductor layer 120 is changed according to a concentration of a designated gas.

Moreover, the resistance of the semiconductor layer 120 is inversely proportional to the concentration of the designated gas. That is, the higher the concentration of the designated gas, the lower the resistance of the semiconductor layer 120 is, and thus the higher the conductivity of the semiconductor layer 120 is. In this way, when the concentration of the designated gas is higher than a predetermined value, the semiconductor layer 120 conducts the first electrode 140 and the second electrode 150, so as to conduct the light-emitting component 130 for light emitting. Thus, a warning that the concentration of the designated gas is too high may be issued to the user.

In the present embodiment, the semiconductor layer 120 is a metal oxide layer, and gas detection is performed by utilizing the fact that conductivity of the metal oxide is significantly changed due to adsorption of the designated gas. For example, when oxygen molecules contact and are adsorbed by a surface of the semiconductor layer 120 in a direction illustrated as an arrow in FIG. 1, since conduction electrons on the surface of the semiconductor layer 120 transfer to the oxygen molecules, the oxygen molecules are present on the surface of the semiconductor layer 120 in the form of chemisorbed anions (O2-). Thus, a depletion layer is formed on the surface of the semiconductor layer 120, so that the resistance of the semiconductor layer 120 is increased and the conductivity thereof is reduced. However, when the concentration of the designated gas (e.g., reducing gas such as liquefied gas, natural gas, organic solvent vapor, carbon monoxide or hydrogen) in the environment increases, the designated gas reacts with oxygen molecules adsorbed by the surface of the semiconductor layer 120 in the direction illustrated as the arrow in FIG. 1, so as to separate the adsorbed oxygen molecules from the surface of the semiconductor layer 120. Accordingly, the designated gas is adsorbed by the surface of the semiconductor layer 120 in the form of positive ions. In this way, the oxygen molecules emit electrons after being separated from the surface of the semiconductor layer 120, and the designated gas also emits electrons after being adsorbed in the form of positive ions. Thus, density of electrons in the semiconductor layer 120 is increased and the resistance of the semiconductor layer 120 is reduced, so that the conductivity of the semiconductor layer 120 is increased, and the first electrode 140 and the second electrode 150 are conducted.

Under such arrangement, in the present embodiment, the designated gas to be detected by the gas detecting device 100 may be selected by changing the material of the semiconductor layer 120. The following Table 1 illustrates a corresponding relationship between materials of the semiconductor layer 120 and the designated gases to be detected by using these materials. In the present embodiment, the material of the semiconductor layer 120 includes an oxide of graphene, tin, zinc, indium, tungsten, magnesium, iron or titanium, etc. Of course, the present embodiment is merely for illustration, and the disclosure is not limited thereto.

TABLE 1

| Material of Semiconductor Layer | Designated Gas |
|---|---|
| Graphene oxide | $NO_2$, $NH_3$, $H_2$, CO, $H_2O$ |
| ZnO | $NO_2$, $NH_3$, $H_2$, $CH_4$, CO, $H_2S$, $O_2$, NO, $H_2O$, ethanol |
| $SnO_2$ | $H_2$, $CH_4$, CO, $SO_2$, $O_2$, $H_2O$, ethanol, $C_2H_2$ |
| $InO_x$ | $NO_2$, $CH_4$, CO, ethanol, $C_2H_4$ |
| $WO_3$ | $NO_2$, $NH_3$, $H_2$, $CH_4$, CO, $SO_2$, $H_2S$, $O_2$, NO, NO, benzene, ethanol, $O_3$, $Cl_2$ |
| MgO | $NO_2$, $SO_2$, $O_2$ |
| $TiO_2$ | $NO_2$, $NH_3$, CO, $H_2O$, $SO_2$, $O_2$ |
| $Fe_2O_3$ | ethanol, methanol, acetone |

Referring to FIG. 1 and FIG. 3 together, in the present embodiment, the light-emitting component 130 is a light-emitting diode including an upper electrode 134, a lower electrode 132 and a light-emitting unit 136, wherein the lower electrode 132 is coupled to the first electrode 140 as shown in FIG. 1, and the upper electrode 134 is coupled to a power supply 170 so as to receive a power supply voltage $V_{dd}$ supplied by the power supply 170. In the present embodiment, the semiconductor layer 120, the first electrode 140 and the second electrode 150 are viewed as a gas detecting module 125 as shown in FIG. 3, wherein the gas detecting module 125 and the light-emitting component 130 are both coupled to the power supply 170. In this way, when the concentration of the designated gas increases so that the resistance of the semiconductor layer 120 is changed as the concentration of the designated gas is changed, the power supply 170 conducts the light-emitting component 130 according to a signal generated by a detecting module, so as to issue to the user the warning that the concentration of the designated gas is too high.

In addition, in other embodiments, the gas detecting module 125 may be additionally coupled to a detecting module configured to detect variation in resistance of the semiconductor layer 120 and to generate a signal accordingly. The power supply 170 is coupled to the detecting module so as to supply the power supply voltage $V_{dd}$ to the light-emitting component 130 according to the signal. In this way, when the change of the resistance of the semiconductor layer 120 is detected as the concentration of the designated gas is changed, the power supply 170 conducts the light-emitting component 130 according to the signal generated by the detecting module, so as to issue to the user the warning that the concentration of the designated gas is too high.

In summary, in the gas detecting device of the disclosure, at least the substrate and the semiconductor layer are formed by 3-D printing. Thus, the bonding strength between the substrate and the semiconductor layer of the gas detecting device is improved. Moreover, the contact surface of the substrate that contacts the user is designed according to the profile of the user's surface and the substrate is printed accordingly. Therefore, the contact surface of the substrate is tightly attached to the user's surface. In addition, the substrate formed by 3-D printing is effectively reduced in thickness thereof. Therefore, the substrate formed by 3-D printing effectively enhances fitness and user comfort of the gas detecting device.

In addition, the material of the substrate includes cellulose nanofibrils which have high structural strength and light weight and are both ductile and strong. Therefore, the substrate printed with cellulose nanofibrils has not only high structural strength but also less weight, and may thus be attached to the user's surface without falling off easily or causing the user discomfort. Moreover, the disclosure utilizes the characteristic that the resistance of the semiconductor layer is changed according to the concentration of the designated gas. When the concentration of the designated gas is higher than the predetermined value, the semiconductor layer conducts the first electrode and the second electrode, so as to conduct the light-emitting component for light emitting, and thereby enable the user to easily interpret a detecting result of the gas detection. Therefore, the disclosure indeed enhances portability and ease of use of the gas detecting device.

Although the disclosure has been disclosed with reference to the above embodiments, it will be apparent to persons of ordinary skill in the art that modifications to the described embodiments may be made without departing from the spirit of the disclosure. Accordingly, the scope of the disclosure will be defined by the attached claims and not by the above detailed descriptions.

What is claimed is:

1. A gas detecting device configured to be attached to a surface, the gas detecting device comprising:
    a substrate comprises a plurality of stacking layers stacked onto one another, a material of the substrate comprising cellulose nanofibrils, wherein the substrate is formed by a three-dimensional (3-D) printing technique, such that a contact surface of the substrate is tightly attached to the surface;
    a semiconductor layer formed on the substrate by the 3-D printing technique;
    a light-emitting component disposed on the substrate;
    a first electrode coupled to the semiconductor layer and the light-emitting component; and
    a second electrode coupled to the semiconductor layer and a ground electrode, both of the first electrode and the second electrode disposed on the semiconductor layer and a gap maintained between the first electrode and the second electrode, wherein a resistance of the semiconductor layer is changed according to a concentration of a designated gas.

2. The gas detecting device according to claim 1, wherein a greatest thickness of the substrate ranges from 10 μm to 100 μm.

3. The gas detecting device according to claim 1, wherein the contact surface is a flat surface, so as to conform to a flat-surface profile of the surface.

4. The gas detecting device according to claim 1, wherein the contact surface is a curved surface so as to conform to a curved-surface profile of the surface.

5. The gas detecting device according to claim 1, further comprising an adhesive layer disposed on the contact surface so as to attach the substrate to the surface.

6. The gas detecting device according to claim 1, wherein the semiconductor layer is a metal oxide layer.

7. The gas detecting device according to claim 1, wherein a material of the semiconductor layer comprises an oxide of graphene, tin, zinc, indium, tungsten, magnesium, iron or titanium.

8. The gas detecting device according to claim 1, wherein the resistance of the semiconductor layer is inversely proportional to the concentration of the designated gas.

9. The gas detecting device according to claim 1, wherein the light-emitting component comprises a light-emitting diode.

10. The gas detecting device according to claim 1, wherein the first electrode, the second electrode and the light-emitting component are formed by the 3-D printing technique.

\* \* \* \* \*